United States Patent [19]

George

[11] Patent Number: 4,486,489
[45] Date of Patent: Dec. 4, 1984

[54] FILMS OF HYDROPHILIC INTERPOLYMERS OF NEUTRALIZED ACRYLIC ACID, HYDROXYALKYL METHACRYLATE OR DIALKYLAMINOALKYL (METH)ACRYLATE AND OPTIONALLY A CROSS-LINKING AGENT

[75] Inventor: Paul J. George, Richfield, Ohio
[73] Assignee: The B. F. Goodrich Company, Akron, Ohio
[21] Appl. No.: 427,325
[22] Filed: Sep. 29, 1982

Related U.S. Application Data

[63] Continuation-in-part of Ser. No. 166,936, Jul. 8, 1980, abandoned.

[51] Int. Cl.$^3$ .................. B32B 00/00; C08F 220/28; C08F 220/36; C08F 220/64
[52] U.S. Cl. .......................... 428/220; 204/159.22; 204/159.23; 524/555; 524/558; 526/75; 526/240; 526/309; 526/311; 526/312; 526/313; 526/317; 604/372
[58] Field of Search ................. 428/220; 526/75, 240, 526/309, 311, 312, 313, 317; 204/159.22, 159.23; 524/555, 558

[56] References Cited

U.S. PATENT DOCUMENTS

| | | | |
|---|---|---|---|
| 4,062,817 | 12/1977 | Westerman | 526/317 |
| 4,066,583 | 1/1978 | Spaulding | 526/317 |
| 4,115,331 | 9/1978 | Tominaga et al. | 526/240 |
| 4,167,464 | 9/1979 | George | 526/240 |

*Primary Examiner*—Harry Wong, Jr.
*Attorney, Agent, or Firm*—Nestor W. Shust; George A. Kap; Carl W. Battle

[57] ABSTRACT

Films of water containing hydrophilic interpolymers prepared by photopolymerization of monomer mixtures comprising partially or fully neutralized acrylic acid, hydroxyalkyl methacrylate or dialkylaminoalkyl (meth-)acrylate and optionally a cross-linking agent. The films are useful as absorbents.

5 Claims, No Drawings

FILMS OF HYDROPHILIC INTERPOLYMERS OF NEUTRALIZED ACRYLIC ACID, HYDROXYALKYL METHACRYLATE OR DIALKYLAMINOALKYL (METH)ACRYLATE AND OPTIONALLY A CROSS-LINKING AGENT

This is a continuation-in-part of my co-pending application Ser. No. 166,936, filed July 8, 1980, now abandoned.

BACKGROUND OF THE INVENTION

A variety of hydrophilic polymers which are useful in the manufacture of water absorbent films and fibers have been reported in the prior art. U.S. Pat. No. 3,915,921 discloses copolymers of unsaturated carboxylic acid monomers with alkyl acrylate esters wherein the alkyl group contains 10 to 30 carbon atoms. However, because of the high Tg of these polymeric materials, it is difficult to extrude them in fiber or film form. Furthermore, films pressed from the powders require high temperatures, the films are brittle and fragile, and have a reduced initial rate of water absorption.

U.S. Pat. No. 4,062,817 discloses polymers of unsaturated copolymerizable carboxylic acids, at least one alkyl acrylate or methacrylate wherein the alkyl group has 10 to 30 carbon atoms and another alkyl acrylate or methacrylate wherein the alkyl group has 1 to 8 carbons. This composition alleviated many of the deficiencies of the earlier compositions. Further improvements in the hydrophilic properties were obtained by compositions disclosed in U.S. Pat. No. 4,066,583. This patent discloses a composition comprising (1) a copolymer of the type disclosed in the '817 patent, except that after copolymerization 30 to 90 percent of the carboxylic groups were neutralized with an alkali metal or ammonia and (2) an aliphatic glycol, a plasticizer which is important in facilitating extrusion of the polymer.

Most recently, U.S. Pat. No. 4,167,464 discloses highly water absorbent polymers obtained by photopolymerizing an alkaline metal salt of acrylic acid, a long chain alkyl acrylate or methacrylate, and a short chain alkyl acrylate or methacrylate in the presence of a photoinitiator.

SUMMARY OF THE INVENTION

A highly water absorbent interpolymer is obtained from a monomer mixture of 65 to 95 weight percent of acrylic acid, 60 to 100% of the carboxylic groups of said acid having been neutralized prior to polymerization with an alkaline metal hydroxide or ammonia, and 5 to 35 weight percent of 2-hydroxyethyl methacrylate or a dialkylaminoalkyl acrylate or methacrylate. The monomer mixture can be spread to the desired thickness and then polymerized upon exposure to a UV light or radiation sources to give a water absorbent film. If photopolymerized, a photoinitiator must be employed.

DETAILED DISCLOSURE

This invention is directed to a water insoluble, flexible, highly water absorbent film having up to 25 mil (0.635 mm) thickness and containing 25 to 45 weight percent of water based on the total weight of the film, said film being prepared by photopolymerizing (1) a monomer mixture consisting essentially of (a) 65 to 95 weight percent of acrylic acid, 60 to 100 percent of the carboxylic groups having been neutralized with an alkali metal hydroxide or ammonia base prior to polymerization, (b) 5 to 35 weight percent of a comonomer selected from the group consisting of 2-hydroxyethyl methacrylate and dialkylaminoalkyl acrylate or methacrylate wherein each alkyl of the dialkyl groups has 1 to 8 carbons and the other alkyl group has 2 to 6 carbons, (c) 0.01 to 5 weight percent, based on the total weight of the monomers, of a photoinitiator, and (d) 0 to 5 weight percent, based on the total weight of the monomers, of a cross-linking agent which contains two or more ethylenic unsaturations, and (2) a sufficient amount of water so that the resulting film contains 25 to 45 weight percent of water.

The polymers of this invention may be prepared with or without a cross-linking agent. When a polyfunctional cross-linking agent is employed it is used in the amount of 0.1 to 5 weight percent. For economic reason it is preferable to use the least amount of a cross-linking agent and it has been found that some of the best compositions are obtained when a cross-linking agent is used in the amount of from 0.1 to 1 percent.

The cross-linking agents that may be employed in this invention are monomeric compounds which contain two or more ethylenically unsaturated groups which can be copolymerized with acrylic acid by UV light. Usually the cross-linking agents have two to six ethylenically unsaturated groups such as allyl, acrylate or vinyl groups. The nature of that portion of the molecule which does not contain ethylenic unsaturation is of no critical consequence as long as it does not possess groups which would interfere with UV polymerization. Usually that part of the molecule is made up of a saturated hydrocarbon chain, a glycol or a polyglycol moiety, an aromatic moiety or cyanurate or isocyanurate ring or other non-polymerizable moieties.

Polyfunctional compounds that may be used as cross-linking agents include, for example, diallyl esters or ethers, allyl or methallyl acrylates and acrylamides, diacrylates and dimethacrylates, divinyl compounds and the like. Illustrative examples of polyfunctional cross-linking agents are polyethyleneglycol diacrylate and dimethacrylate, ethylene glycol dimethacrylate, tetraethyleneglycol diacrylate, 1,3-butyleneglycol dimethacrylate, diethyleneglycol divinyl ether, trimethylolpropane diallyl ether, divinyl benzene, trimetnylolpropane triacrylate, trimethylolpropane trimethacrylate, triallyl cyanurate, pentaerythritol triacrylate, diallyl itaconate, methylene bis(acrylamide), allyl pentaerithritol, allyl sucrose, 1,6-hexanediol diacrylate, tetramethylene glycol diacrylate and dimethacrylate, ethylene glycol diacrylate, triethyleneglycol dimethacrylate and the like.

Another class of cross-linking agents is acrylates and methacrylates of polyvalent metals, especially useful being those that have two or three valences, such as calcium, magnesium and aluminum. Typical examples of such cross-linking agents are calcium diacrylate and dimethacrylate, magnesium diacrylate and dimethacrylate, aluminum triacrylate and trimethacrylate and the like. The metal acrylates of methacrylates can be added to the monomer mixture in the same manner as the other cross-linking agents. However, the metal acrylates can also be made in situ by adding the metal hydroxide, e.g., calcium hydroxide, magnesium hydroxide or aluminum hydroxide, to acrylic acid, preferably before neutralization.

At least 60 percent of the carboxylic groups must be neutralized prior to polymerization and preferably 70 percent of said groups should be neutralized. A very useful degree of neutralization is 60 to 85 percent because the resulting polymers have a good balance of properties. Neutralization is accomplished by the addition of an alkali metal hydroxide or ammonium hydroxide to acrylic acid. Typical and practical examples of the neutralizing agents are sodium and potassium hydroxide and ammonium hydroxide.

The monomer mixture is dispersed in water and the amount of water used is of critical importance. The amount of water required depends on the degree of neutralization. Generally, the higher the degree of neutralization the greater the amount of water is required. As to the effect of the cation, the amount of water required depends on the solubility of the resulting salt. For example, the potassium salt of acrylic acid is more soluble in water than the sodium salt and therefore less water would be required if potassium hydroxide is used for neutralization. Similarly, the ammonium salt of acrylic acid is more soluble than the potassium salt and thus even less water is required if ammonium hydroxide is used for neutralization.

However, there is another important consideration in determining the amount of water required. In order to have the required balance of physical properties, the resulting cross-linked polymer must possess 25 to 45 weight percent of water. Therefore, the amount of water present in the monomer mixture must be such that the resulting film would contain the noted requisite moisture content. Based on the above discussion, one skilled in the art would have little difficulty in establishing how much water would be required in a particular situation. It was found that the amount of water required was such that the resulting solution or dispersion generally contains 25 to 45 weight percent based on the total weight of the monomer mixture and water.

The monomer mixture can be copolymerized by subjecting it to UV light. The mixture can be spread on a surface to the desired thickness, e.g., 1 mil (0.0254 mm) to 25 mil (0.635), and then subjected to UV light for a short time, e.g., one second to several minutes. The actual length of irradiation will depend on a number of factors, such as the thickness of the monomer, film the distance from and the intensity of the source of irradiation, the specific monomers employed and the ratio of such monomers to each other, the presence or absence of additional comonomers and the nature and the amount of the photoinitiator employed. The type of photoinitiator employed will depend at least in part on the type of UV irradiation employed (particularly its wavelength) since various photoinitiators may be decomposed by UV light of different wavelengths.

In order to effect quick and efficient polymerization under UV light, 0.01 to 5 weight percent of a pnotoinitiator, preferably 0.1 to 5 percent and more preferably 0.2 to 1.0 weight percent, must be incorporated into the monomer mixture. Any compound which dissociates into free radicals when exposed to UV radiation can be employed. There are many known photoinitiators or photosensitizers such as acetophenone, propiophenone, benzophenone, xanthone, fluorenone, benzaldehyde, fluorene, anthraquinone, triphenylamine, carbazole, 3- or 4-methylacetophenone, 3- or 4-pentylacetophenone, 3- or 4-methoxyacetophenone, 3- or 4-bromoacetophenone, 3- or 4-allylacetophenone, p-diacetylbenzene, 3- or 4-methoxybenzophenone, 3- or 4-methylbenzophenone, 3-or 4-chlorobenzophenone, 4,4'-dimethoxybenzophenone, 4-chloro-4'-benzylbenzophenone, 3-chloroxanthone, 3,9-dichloroxanthone, 3-chloro-8-nonyl-xanthone, 3-methoxyxanthone, 3-iodo-7-methoxyxanthone, 2,2-dimethoxyacetophenone, 2,2-dimethoxy-2-phenylacetophenone, 2,2-diethyoxyacetophenone, 2,2-di-butoxyacetophenone, 2,2-dihexoxyacetophenone, 2,2-di(2-ethylhexoxy) acetophenone, 2,2-diphenoxyacetophenone, benzoin, ethyl benzoin ether, ethyl bonzoin ether, isopropyl benzoin ether, butyl benzoin ether, isobutyl benzoin ether, bonzoin acetate, benzoin phenyl carbamate α,α-diethoxyacetophenone, α,α-di-ethoxy-α-phenyl acetophenone, α,α-dimethoxy-α-phenyl- acetophenone, 4,4'-dicarboethoxybenzoinethyl ether, α-chloroacetophenone, α-bromoacetophenone, benzoin phenyl ether, α-methylbenzoin ethyl ether, benzoin acrylate, α-methylbonzoin methyl ether,α,α,α-trichloroacetophenone, o-bromoacetophenone, cumeme hydroperoxide, benzoyl peroxide, tert-butyl perbenzoate, α,α-azobisisobutyronitrile, phenyl disulfide, chloromethylbenzanthrone, chloromethylanthraquinone, chloromethylnaphthalene, bromomethylbenzanthrone, bromomethylanthraquinone, bromomethylnaphthalene, and the like.

In addition to the photoinitiator it may be advantageous to employ also from 0.1 to 5.0 percent of an air cure promoter. Illustrative examples of air cure promoters are Michler's ketone (4,4'-dimethylaminobenzophenone), diethanolamine, methyl diethanolamine, ethyl p-dimethylaminobenzoate, and the like.

The monomer mixtures are prepared as aqueous dispersions which eliminates the need for organic solvents This avoids the pollution problems caused by the removal of organic solvents or the cost associated with the removal of the pollutants. In order to obtain a stable homogeneous dispersion of the monomers, it is preferred that the aqueous dispersions contain 0.01 to 5%, and preferably 0.1 to 1%, of a surface active agent such as an anionic, amphoteric, or non-ionic dispersing agent or a mixture of dispersants. Useful anioinic dispersing agents include alkali metal or ammonium salts of the sulfates of alcohols having from 8 to 18 carbon atoms such as sodium lauryl sulfate; ethanolamine lauryl sulfate, ethylamine lauryl sulfate; alkali metal and ammonium salts of sulfonated petroleum and paraffin oils; sodium salts of aromatic sulfonic acids such as dodecane-1-sulfonic acid and octadecane-1-sulfonic acid; aralkyl sulfonates such as sodium isopropyl benzene sulfonate, sodium dodecyl benzene sulfonate and sodium isobutyl naphthalene sulfonate; alkali metal and ammonium salts of sulfonated dicarboxylic acid esters such as sodiumdioctyl sulfosuccinate, disodium-n-octadecyl sulfosucciante; alkali metal or ammonium salts of free acid of complex organic mono and diphosphate esters, sulfosuccinic acid derivatives (AEROSOL dispersants), organic phosphate esters (GAFAC dispersants) and the like. Nonionic dispersants such as octyl or nonylphenyl polyethoxyethanol as well as the PLURONIC and the TRITON dispersants may also be used. Also useful are amphoteric dispersants such as dicarboxylic coconut derivatives (MIRANOL). Further examples of useful dispersants are those disclosed beginning on page 102 in J. Van Alphen's "Rubber Chemicals", Elsevier Publishing Company, 1956.

The copolymers of this invention can be photopolymerized in a film form. The resulting film is an elastic, flexible material that has an appreciable degree of strength. If a fine, flaky form is desired, the film can be converted to such a form by drying and then pulverizing or grinding it in standard equipment.

The most important property of the films of this invention is their ability to absorb and retain, even if some pressure is applied, large amounts of water or aqueous ionic solutions such as body fluids. Such films will generally absorb from 15 times their weight of ionic solutions containing up to 1 percent of sodium chloride or of body fluids such as urine, and from 100 to 1500 times their weight of distilled water.

As water absorbent materials, the films find many uses. They are of particular utility in the disposable non-woven industry where there is need for polymers which will absorb and retain water and ionic physiological fluids. An important feature of these polymers is their enhanced thickening property even in the presence of a salt. Specific applications include disposable diapers, medical-surgical supplies and personal care products. Such applications require a polymer which must imbibe the liquid to be absorbed rapidly and be a polymer that will not dissolve. Further, the fluid must be immobilized or congealed in some way to be retained. The materials may also be used as suitable additives to greatly increase the absorptive power of conventional absorbents such as cotton, wood pulp and other cellulosic absorbents used in applications sucn as wiping cloths, surgical sponges catamenial devices. and the like. In a specific application, for example, a disposable diaper, there is an inner layer of a soft absorbent nonwoven material that absorbs and passes urine to an inner layer of fluffy fibrous absorbent material, wherein during the construction of this non-woven fiber aggomerates or fibers of the polymers of this invention may be included and an additional impervious plastic layer, as polyethylene. A film of the copolymers of this invention may be used between the outer plastic layer and the inner fluffy absorbent layer. Use of the polymers of this invention can result in reduction in the bulk size of many disposable non-wovens.

A particularly important utility for the polymeric films of this invention is their use in burn wound dressings. It is important that such dressings promote healing and be easily removable without sticking to the injured part of the skin and be permeable to air. The polymeric films of this invention nave a combination of properties that make them particularly useful in such application, especially the ability to retain moisture in various proportions. The absorbent properties of said polymeric films make them useful in other medical applications such as surgical absorbers where the quick removal of body fluids is important. Such films are also very useful in the removal of topical body fluids such as perspiration.

The instant copolymers can also be used as flocculants in water treatment, in metallurgical processes, in ore beneficiation and flotation, in agricultural applications such as in soil treatment or seed coating or in any applications where the inherent properties of the polymer are desirable, such as its thickening property in an aqueous medium.

To prepare the polymers of this invention, acrylic acid, a comonomer, a cross-linking agent, water, a dispersant and a photoinitiator are mixed in a vessel. Then a film is produced from the monomer mixture which, upon exposure to UV light, is rapidly polymerized. The various steps in the procedures are described in greater detail below.

Monomer Mixture Preparation: The monomer mixture can be prepared by the following procedure. One can dissolve a previously prepared neutralized acrylic acid in water to which is then added a comonomer and a dispersant. To the aqueous solution is then added a cross-linking agent which may already contain a photoinitiator. Photoinitiator may also be added to the unneutralized acrylic acid.

Film Preparation: The aqueous monomer dispersion is spread to a desired thickness (e.g., by the use of Boston-Bradley adjustable blade, by spraying or other known means) on a suitable substrate (e.g., Mylar, polyethylene, paper, etc.). The liquid film is then exposed to UV irradiation which polymerizes the monomer mixture into a soft, pliable form. If desired, this film can be dried in an oven at about 50° C. for 1 to 15 min. After drying, the film may still retain some flexibility or become brittle and flaky, depending on the length of drying.

To further illustrate the present invention, the following examples are presented. The copolymers and the films were prepared according to the procedures described above. The copolymers of Examples 1 and 2, presented in Table I, have been photopolymerized using QC 1202 Processor manufactured by Radiation Polymer Company (with belt speed of 0 to 1000 ft/min.-304.8 m/min.) having 2 medium pressure quartz mercury vapor lamps at 200 watts/lineal inch (watts/lineal 2.54 cm.). The distance from tne lamps to the film was 15 cm. and the exposure time was 20 sec. at belt speed of 20 ft/min. (6 m/min.).

Comonomers employed in the Examples and identified in Table I by capital letters A and B, are identified below:

A—2-Hydroxyethyl metnacrylate
B—Dimethylaminoethyl acrylate

TABLE I

|  | Example No. | |
| --- | --- | --- |
|  | 1 | 2 |
| Sodium hydroxide | 43.6 g | 43.6 g |
| % Neutralization | 95% | 95% |
| Water | 152.0 g | 152.0 g |
| Acrylic acid | 83.0 g | 83.0 g |
|  | A | B |
| Comonomer | 17.0 g | 17.0 g |
| AEROSOL A102[1] | 1.24 g | 1.24 g |
| IRGACURE 651[2] | 0.62 g | 1.2 g |

[1]AEROSOL A102 is disodium ethoxylated alcohol half ester of sulfosuccinic acid, a dispersant.
[2]IRGACURE 651 is 2,2-dimethyloxy-2-phenyl-acetophenone, a photoinitiator.

Copolymers having substantially the same properties are ootained wnen in some of the above compositions potassium hydroxide is employed in place of sodium or ammonium hydroxide, 2,2-diethyoxyacetophenone in place of IRGACURE 651 and an oligomeric surfactant POLYWET KX-3 (from Uniroyal) or TRITON N-111 (nonylphenoxy polyethoxy ethanol) in place of AEROSOL A102.

A number of tests are available to determine the absorbency of, a material. Following are descriptions of the two test procedures which were employed in evaluating absorbency of the interpolymers of this invention.

Static Test (ST)—A weighed film sample is immersed in a test liquid for 10 minutes. It is then removed from the liquid, the excess liquid drained for a few seconds and then shaken lightly several times. The swelled sample is weighed again to determine the weight of liquid absorbed by the polymer.

Demand Wettability Test (DWT)—A test diaper is constructed from a 4 inch diameter pad (10.16 cm.) using materials from a commercial diaper. A film prepared from a polymer to be tested for absorbency is placed in the center of the test diaper between two layers of fluff (wood pulp). A diaper without the polymer film is used as a blank. The demand-wettability apparatus is a burette filled with the test fluid and firmly stoppered at the top, with an air bleed on the side, and a delivery orifice on the bottom connected by a flexible tube to the sample holder. The sample holder has an opening in the center which is connected to the flexible tube that leads to the delivery orifice of the burette. The sample holder is level with the air bleed opening in the burette. With this closed-system arrangement the fluid in the flexible tube that comes up to the opening in the sample holder is at zero pressure. Thus, when the test diaper is placed on the sample holder over the opening, it will absorb the fluid on its own through wicking action. The sample's own absorbent powder will determine the rate and amount of fluid that will be withdrawn from the burette. The amount of fluid withdrawn at any given time can be easily read from the burette calibration. An additional feature is that absorbency can be measured against a range of pressures that can be obtained by placing various weights on top of the test diaper. Such pressures are intended to simulate the pressures applied on a diaper in actual use.

This test is described in greater detail by Lichstein, "Demand Wettability, a New Method for Measuring Absorbency Characteristics of Fabrics", Symposium Papers-INDA Technical Symposium, 1974, pp. 129-142.

Compression Test (CT)—This test is a follow-up test to the Demand-Wettability Test (DWT). After the sample has absorbed the liquid against a lower pressure in a DWT, it is removed from the DWT apparatus and placed atop a porous filter funnel. The sample is then subjected to 1.5 psi (0.105 kg/cm$^2$) of pressure for 1 minute and the amount of liquid that is squeezed from the sample is measured. Said pressure corresponds to the maximum pressure that is exerted on portions of a diaper when a toddler is picked up or held. This is 10 to 15 times the pressure that the diaper normally would experience. The sample is then weighed to determine the amount of fluid in grams retained per one gram of polymer.

In Table II below is presented data showing the absorbency properties of the copolymer of this invention. The polymer number in the Table corresponds to the example describing the preparation of that specific polymer in Table I.

TABLE II

| Polymer | ST (g/g) | DWT (ml/g) | CT (g/g) |
|---|---|---|---|
| 1 | 26 | — | — |
| 2 | — | 33 | 29 |

I claim:
1. A water insoluble, flexible, highly water absorbent polymeric film having up to 25 mil thickness and containing 25 to 45 weight percent of water, said film being prepared by photopolymerizing a monomer mixture consisting of
   (a) 65 to 95 weight percent of acrylic acid, 60 to 100 percent of the carboxylic groups having been neutralized with an alkali metal hydroxide or ammonia base prior to polymerization,
   (b) 5 to 35 weight percent of a comonomer selected from the group consisting of 2-hydroxyethyl methacrylate and dialkylaminoalkyl acrylate or methacrylate wherein each alkyl of the dialkyl groups has 1 to 8 carbons and the other alkyl group has 2 to 6 carbons, and
   (c) 0 to 5 weight percent, based on the weight of the monomers, of a cross-linking agent which contains two or more ethylenic unsaturations in the presence of 0.01 to 5 weight percent, based on the total weight of the monomers, of a photoinitiator and a sufficient amount of water so that the resulting polymeric film contains 25 to 45 weight percent of water.

2. A polymeric film of claim 1, wherein 60 to 85% of the carboxylic groups are neutralized.

3. A film of claim 1, wherein said photoinitiator is used in the amount of from 0.1 to 5 weight percent.

4. A film of claim 1 containing 0.1 to 5 weight percent of said cross-linking agent selected from the group consisting of
   1,3-butyleneglycol dimethacrylate,
   polyethyleneglycol diacrylate,
   polyethyleneglycol dimethacrylate,
   ethyleneglycol dimethacrylate,
   diethyleneglycol divinyl ether,
   tetraethyleneglycol diacrylate,
   trimethylolpropane trimethacrylate,
   triallyl isocyanurate,
   diallyl itaconate,
   allyl methacrylate,
   allyl pentaerythritol,
   N,N'-methylenebis(acrylamide), and
   calcium, magnesium and aluminum acrylate and methacrylate.

5. A film of claim 1 wherein in its preparation said photoinitiator is selected from the group consisting of
   2,2-dimethoxy-2-phenylacetophenone,
   N,N'-bis(diethylamino)benzophenone,
   ethyl p-dimethylamino benzoate and benzophenone,
   a benzoin ether and a mixture thereof.

* * * * *